US00PP08844P

United States Patent [19]

van Dordrecht

[11] Patent Number: Plant 8,844

[45] Date of Patent: Jul. 19, 1994

[54] SPATHIPHYLLUM PLANT—CERES CULTIVAR

[75] Inventor: Erik van Dordrecht, De Kwakel, Netherlands

[73] Assignee: Gebr. Braam BV, De Kwakel, Netherlands

[21] Appl. No.: 38,690

[22] Filed: Mar. 29, 1993

[51] Int. Cl.[5] ..... A01H 5/00

[52] U.S. Cl. ..... Plt./88.1

[58] Field of Search ..... Plt. 88.1

*Primary Examiner*—James R. Feyrer

*Attorney, Agent, or Firm*—Burns, Doane, Swecker & Mathis

[57] ABSTRACT

A new and distinct Spathiphyllum hybrid cultivar of the Mauna Loa type is provided. The new cultivar was produced during the course of a planned breeding program wherein the Pallas cultivar (non-patented in the United States) was crossed by a unnamed seedling of the Mauna Loa type (non-patented in the United States). The new cultivar when compared to its Pallas parent exhibits a smaller more compact growth habit, forms leaves that are narrower, flowers sooner, exhibits leaves that possess a silk-matte finish, forms a geniculum that commonly is more bent, and forms a very sturdy flower stem. The new cultivar serves well as an attractive ornamental pot plant and has been named the Ceres cultivar.

1 Drawing Sheet

SUMMARY OF THE INVENTION

The new cultivar of the present invention was the product of a planned breeding program that was carried out at the nursery of Gebr. Braam B.V. located at De Kwakel, The Netherlands. The female parent was a registerd and commercially grown clone owned by Gebr. Braam B.V. known as the Pallas cultivar. Such female parent was of the Mauna Loa type and was non-patented in the United States. The male parent was an unnamed seedling of the Mauna Loa type of unknown parentage. Such male parent also was non-patented in the United States. Neither parent was commercially available in the United States prior to the filing date of the application that matured into this patent. The parentage of the new cultivar of the present invention can be summarized as follows:

PALLAS × Unnamed Seedling.

The initial selection of the new cultivar from among the resulting progeny was conducted during October, 1989.

It was found that the new cultivar of the present invention can be readily distinguished from its Pallas cultivar parent and possessed the following combination of characteristics when grown under greenhouse conditions at De Kwakel, The Netherlands:

(a) exhibits a smaller and more compact (i.e., more dense) growth habit of lesser width than the Pallas cultivar, (b) forms leaves that are narrower (i.e., smaller) than those of the Pallas cultivar, (c) flowers sooner and more frequently than the Pallas cultivar, (d) forms a mature plant that lacks a pronounced main shoot with ground shoots having approximately the same size as the central shoot when the first flower appears, (e) exhibits leaves that possess a silk-matte surface appearance that can be compared to the slightly more glossy leaves of the Pallas cultivar, (f) commonly forms a geniculum that is more curved than that of the Pallas cultivar, and (g) forms a very sturdy erect flower stem.

Other plants resulting from the breeding program lacked this combination of characteristics and particularly the smaller compact growth habit (as illustrated).

The new cultivar has been continuously evaluated for its performance since the time of its initial selection. The first asexual propagation of the new cultivar was conducted during January 1990. The characteristics of the new cultivar have been found to be stably manifest in succeeding generations following such asexual propagation by cuttings and tissue culture carried out at De Kwakel, The Netherlands.

The new Spathiphyllum plant of the present invention has been named the Ceres cultivar.

BRIEF DESCRIPTION OF THE PHOTOGRAPH

FIG. 1 shows a typical flowering plant of the new cultivar at the age of seven months when grown in a greenhouse at De Kwakel, The Netherlands. The daytime temperature was approximately 21.5° C. with provision for the greenhouse windows to open when a temperature of 23° C. was reached. The night temperature was approximately 19° C. with provision for the greenhouse windows to open when a temperature of 25° C. was reached. The daytime relative humidity was approximately 80 percent, and the night relative humidity was approximately 70 percent. The attractive compact growth habit, leaf configuration, leaf venation, flower form, and stiff erect flower stem are readily observable.

DETAILED DESCRIPTION OF THE NEW CULTIVAR

Figure 1:
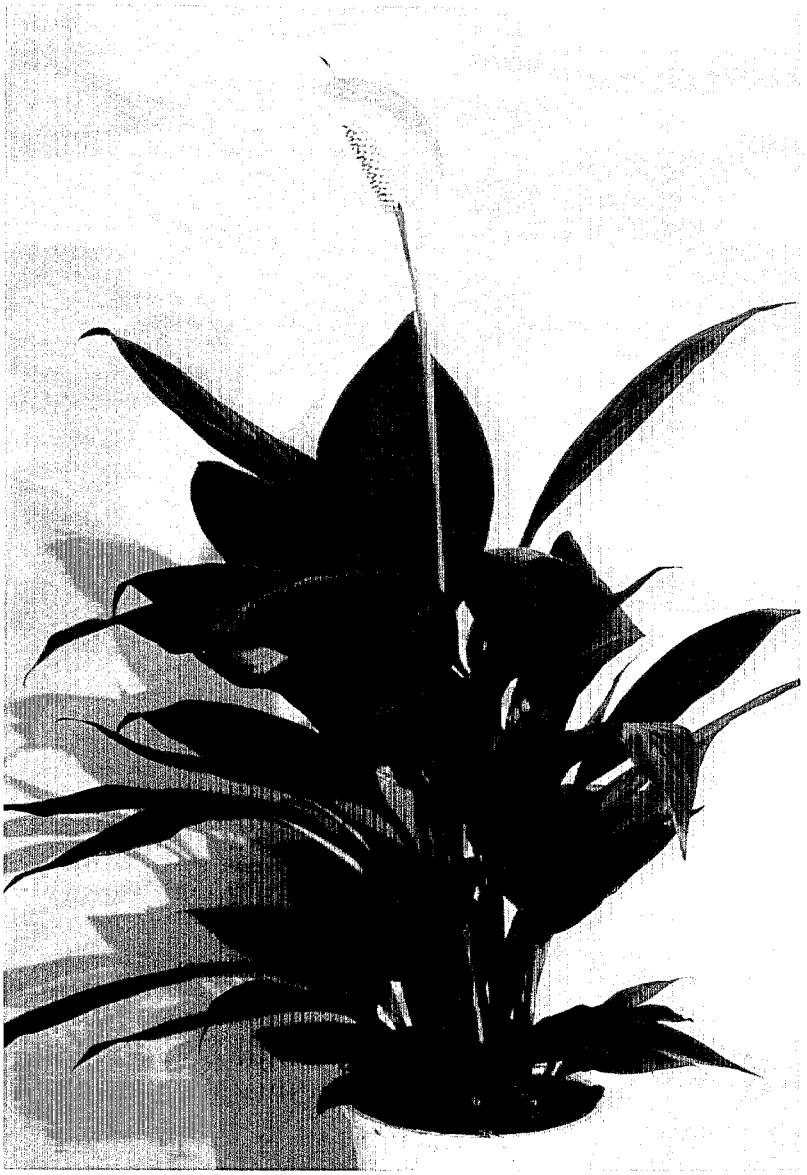

The following description of the new cultivar of Spathiphyllum is based upon the observation of plants growing in pots under greenhouse conditions at De Kwakel, The Netherlands. Color is identified by reference to The R.H.S. Colour Chart of The Royal Horticultural Society, London.

Classification:

*Botanical.*—Spathiphyllum hybrid, cv. Ceres.

*Commercial.*—Spathiphyllum, of the Mauna Loa type.

Parentage:

*Female parent.*—Pallas cultivar of the Mauna Loa type.

*Male parent.*—Unnamed seedling of the Mauna Loa type.

Propagation: The preferred mode of vegetative propagation is by tissue culture.

Plant: The new cultivar when mature and grown in a 13 cm. pot commonly will assume a height of approximately 40 cm. and a width of approximately 35 cm. In contrast the Pallas cultivar under the same growing conditions commonly will assume a height of approximately 40 cm. coupled with a substantially greater width of approximately 50 cm. The plant sizes will vary with the latitude where grown as will be apparent to those experienced in the growing of Spathiphyllum plants. For instance, relatively larger plant sizes are achieved at more southern latitudes than experienced in The Netherlands. The canopy of the new cultivar is more dense with smaller leaves than that of the Pallas cultivar. In populations of mature plants the higher leaf density and smaller leaf size of the new cultivar when compared to the Pallas cultivar is readily apparent. Mature plants of the new cultivar do not exhibit a prominent central or main shoot. For instance, when the first flower appears on the new cultivar, the ground shoots are of approximately the same size as the central or main shoot. On the contrary, when a flower first forms on the Pallas cultivar, a pronounced main shoot commonly is present which is surrounded by some ground shoots that tend to be much less developed than the main shoot. Also, the ground shoots of the new cultivar tend to be somewhat spaced at a distance from the main shoot at ground level while those of the Pallas cultivar tend to be positioned more adjacent the main shoot.

Leaves:

*Form.*—The leaf blade is ovate with a cuspidate-acuminate tip. The leaf margin of the new cultivar is entire.

*Size.*—The length of a mature leaf commonly is approximately 18 to 25 cm. This can be compared to a common mature leaf length of approximately 25 to 35 cm. (approximately 40 cm. maximum) exhibited by the Pallas cultivar. The leaf width of the new cultivar commonly is substantially narrower than that of the Pallas cultivar. For instance, the leaf length to width ratio for the new cultivar commonly is approximately 2.75:1, while the leaf length to width ratio of the Pallas cultivar under the same growing conditions commonly is approximately 2:1.

*Petiole.*—Commonly Green Group 137B, approximately 24 to 30 cm. in length and approximately 3 to 4 mm. in width when measured above the wings on a mature plant, the wings commonly are present along the entire length of the petiole on a young plant, the wings commonly are present along approximately 75 percent of the petiole as the plant approaches maturity during the transitional growth phase, the wings commonly are present along approximately 60 percent of the petiole when the plant is mature, and the wings commonly measure approximately 5 to 7 mm. at each side of the petiole.

*Geniculum.*—Commonly is more curved than that of the Pallas cultivar. On young plants of the new cultivar all genicula tend to be curved and to form angles of approximately 20 to 50 degrees. On mature plants of the new cultivar approximately one-half of the leaves have either uncurved or slightly curved genicula which exhibit angles of approximately 10 degrees, and approximately one-half of the leaves have curved genicula which exhibit angles of approximately 15 to 50 degrees. On mature plants of the Pallas cultivar the genicula tend to be uncurved or slightly curved (i.e., approximately 10 degrees). The diameters of the genicular of mature plants of the new cultivar commonly are 2.9 to 4.9 mm. with a mean of approximately 3.8 mm., while those of the Pallas cultivar commonly are 4.5 to 6.2 mm. with a mean of approximately 5.3 mm.

*Veins.*—It is found following detailed observation that the venation tends to be somewhat variable (as illustrated). More specifically, some veins are alternate, and some are opposite or nearly opposite. The leaf areas to right and left of the main vein of the new cultivar tend to be substantially symmetrical with the exception of the area near the leaf tip. The area at the leaf tip tends to be asymmetrical. On the contrary, the leaf areas to right and left of the main vein of the Pallas cultivar tend to be clearly asymmetrical throughout the leaf. The main vein of the leaves of the new cultivar is substantially straight and is substantially uncurved. The main vein of the Pallas cultivar tends to be curved.

*Color.*—Generally approaches Green Group 138A on the upper surface and lighter on the under surface (i.e., near Green Group 138B to 138C) with the veins appearing darker in coloration on the under surface.

*General appearance.*—Commonly possess a silk-matte surface appearance that can be compared to the slightly more glossy leaves of the Pallas cultivar.

Flowers: The new cultivar, in the absence of the application of a growth regulator commonly flowers in 7 months from the time of potting while the Pallas cultivar commonly requires 8 to 9 months for the onset of flowering in the absence of the application of a growth regulator. The flowers are borne on an erect very sturdy stem (as illustrated). Also, the new cultivar flowers more readily and frequently than the Pallas cultivar with the typial flowering duration for the new cultivar being approximately 4 to 5 weeks. The flowers and reproductive organs tend to be typical of the species. The new cultivar is fertile, both male and female.

*Size.*—The spathe commonly measures approximately 9 to 16 cm. in length (e.g., approximately 15 cm.) and approximately 5 to 12 cm. in width (e.g., approximately 7.5 cm.). This can be compared to a spathe length of approximately 12 to 20 cm. and width of approximately 6 to 11 cm. for the Pallas cultivar. The spadix commonly measures approximately 4.5 to 7 cm. in length and approximately 12 to 15 mm in diameter.

*Color.*—The spathe commonly assures a coloration of White Group 155D with the color turning to green after approximately four weeks and the spathe commonly lasts for several months. The spadix commonly assumes a coloration of Yellow-White Group 158B with the color turning to dark green after approximately four weeks. The flowers commonly assume a coloration of Green Group 143A, but are slightly yellower.

*Form.*—When the spathe is flattened it tends generally to form the shape of an egg. This can be contrasted to the spathe configuration of the Pallas cultivar that tends to be more ovate. The spathe tends to be asymmetrical especially at the base. Commonly there is a distinct curve on one side or the other of the spathe as it meets the peduncle. The angle of the spadix to the peduncle commonly is approximately 20 degrees; however, it sometimes has been observed to approach 5 degrees. The edge of the spathe as seen from the side tends to run parallel to the longitudinal axis of the spadix.

*Peduncle.*—The length commonly is approximately 40 to 50 cm. during March–April, and approximately 45 to 55 cm. during August–September. The diameter commonly is approximately 4 to 5 mm.

Disease resistance: When the new cultivar is compared to the Petite cultivar that is well-known in the United States, it is found to be more resistant to Phytophtora and other common root diseases.

I claim:

1. A new and distinct cultivar of Spathiphyllum having the following combination of characteristics:

(a) exhibits a smaller and more compact growth habit of lesser width than the Pallas cultivar,
(b) forms leaves that are narrower than those of the Pallas cultivar,
(c) flowers sooner and more frequently than the Pallas cultivar,
(d) forms a mature plant that lacks a pronounced main shoot with ground shoots having approximately the same size as the central shoot when the first flower appears,
(e) exhibits leaves that possess a silk-matte surface appearance that can be compared to the slightly more glossy leaves of the Pallas cultivar,
(f) commonly forms a geniculum that is more curved than that of the Pallas cultivar, and
(g) forms a very sturdy erect flower stem;

substantially as illustrated and described.

* * * * *